United States Patent
Schulte et al.

(10) Patent No.: US 7,223,878 B2
(45) Date of Patent: May 29, 2007

(54) REDUCTION OF CONCENTRATION OF INORGANIC BY-PRODUCTS AND ORGANOMETALLIC BY-PRODUCTS IN THE PREPARATION OF METALLOCENES AND ECONOMICAL RECOVERY OF THE STARTING MATERIALS USED

(75) Inventors: Jörg Schulte, Frankfurt (DE); Jörg Schottek, Frankfurt (DE)

(73) Assignee: Basell Polyolefine GmbH, Frankfurt (DE)

( * ) Notice: Subject to any disclaimer, the term of this patent is extended or adjusted under 35 U.S.C. 154(b) by 134 days.

(21) Appl. No.: 10/478,666

(22) PCT Filed: May 18, 2002

(86) PCT No.: PCT/EP02/05513

§ 371 (c)(1),
(2), (4) Date: Nov. 24, 2003

(87) PCT Pub. No.: WO02/096920

PCT Pub. Date: Dec. 5, 2002

(65) Prior Publication Data

US 2004/0176624 A1    Sep. 9, 2004

(30) Foreign Application Priority Data

May 29, 2001   (DE)   ................. 101 26 265

(51) Int. Cl.
C07F 17/00    (2006.01)
B01J 31/00    (2006.01)

(52) U.S. Cl. .................... 556/11; 556/12; 556/43; 556/47; 556/53; 502/103; 526/943

(58) Field of Classification Search ............ 556/11, 556/12, 43, 47, 53; 502/103; 526/943
See application file for complete search history.

(56) References Cited

U.S. PATENT DOCUMENTS

| 4,650,895 | A | 3/1987 | Kadokura et al. ........... 556/182 |
| 4,752,597 | A | 6/1988 | Turner .......................... 502/104 |
| 5,017,714 | A | 5/1991 | Welborn, Jr. ................. 556/12 |
| 5,103,030 | A | 4/1992 | Rohrmann et al. ........... 556/12 |
| 5,278,264 | A | 1/1994 | Spaleck et al. .............. 526/127 |
| 5,304,614 | A | 4/1994 | Winter et al. ................ 526/127 |
| 5,328,969 | A | 7/1994 | Winter et al. ................ 526/127 |
| 5,329,033 | A | 7/1994 | Spaleck et al. .............. 556/33 |
| 5,455,366 | A | 10/1995 | Rohrmann et al. ............ 556/8 |
| 5,565,534 | A | 10/1996 | Aulbach et al. ............. 526/160 |
| 5,679,812 | A | 10/1997 | Winter et al. ................ 556/7 |
| 5,679,814 | A | 10/1997 | Strickler et al. ............. 556/11 |
| 5,710,297 | A | 1/1998 | Weller et al. ................. 556/11 |
| 5,731,254 | A | 3/1998 | Winter et al. ............... 502/117 |
| 5,770,752 | A | 6/1998 | Kaufmann et al. ........... 556/11 |
| 5,770,753 | A | 6/1998 | Kuber et al. ................. 556/11 |
| 5,786,432 | A | 7/1998 | Kuber et al. ................ 526/127 |
| 5,830,821 | A | 11/1998 | Rohrmann et al. ......... 502/117 |
| 5,840,644 | A | 11/1998 | Kuber et al. ............... 502/117 |
| 5,840,948 | A | 11/1998 | Rohrmann et al. ........... 556/11 |
| 5,852,142 | A | 12/1998 | Rohrmann et al. ......... 526/127 |
| 5,990,254 | A | 11/1999 | Weller et al. ............... 526/160 |
| 6,051,727 | A | 4/2000 | Kuber et al. ................. 556/11 |
| 6,255,506 | B1 | 7/2001 | Kuber et al. ................. 556/11 |

FOREIGN PATENT DOCUMENTS

| DE | 195 47 248 | 6/1997 |
| EP | 129 368 | 12/1984 |
| EP | 336 128 | 10/1989 |
| EP | 387 690 | 9/1990 |
| EP | 530 647 | 3/1993 |
| EP | 537 686 | 4/1993 |
| EP | 545 304 | 6/1993 |
| EP | 549 900 | 7/1993 |
| EP | 561 479 | 9/1993 |
| EP | 576 970 | 1/1994 |
| EP | 632 063 | 1/1995 |
| EP | 659 758 | 6/1995 |
| EP | 661 300 | 7/1995 |
| EP | 780 396 | 6/1997 |
| WO | 98/22486 | 5/1998 |
| WO | 99/52919 | 10/1999 |

OTHER PUBLICATIONS

Organikum, 15th revised Ed., Berlin 1981, p. 226.
Angew.Chem.1995, 107,1255-1283, Brintzinger et al. 1255-1283.
Angew.Chem.Int. Ed.Engl.1995,34,1143-1170.
Chemie, Aulbach et all, 28 1994/Nr.4, 197-208.

Primary Examiner—Porfirio Nazario-Gonzalez
(74) Attorney, Agent, or Firm—Novak Druce & Quigg, LLP

(57) ABSTRACT

A process for separating inorganic and organometallic by-products from a mixture comprising at least one organometallic transition metal compound as product and at least one organometallic by-product and at least one inorganic by-product as by-products comprises the steps A) admixing the mixture comprising the product, the organometallic by-product and the inorganic by-product with a mixture comprising at least one polar organic extractant and water and separating off the undissolved residue, B) washing the residue from step A) with a nonpolar organic extractant or a mixture comprising at least one nonpolar organic extractant and at least one aprotic polar organic solvent and C) drying the residue which has been washed in step B) and comprises the organometallic transition metal compound.

11 Claims, No Drawings

REDUCTION OF CONCENTRATION OF INORGANIC BY-PRODUCTS AND ORGANOMETALLIC BY-PRODUCTS IN THE PREPARATION OF METALLOCENES AND ECONOMICAL RECOVERY OF THE STARTING MATERIALS USED

The present invention relates to a process for separating inorganic and organometallic by-products from a mixture comprising at least one organometallic transition metal compound as product and at least one organometallic by-product and at least one inorganic by-product as by-products.

Metallocenes can, if appropriate in combination with one or more cocatalysts, be used as catalysts for the polymerization and copolymerization of olefins. In particular, halogen-containing metallocene complexes are used as catalyst precursors which can be converted, for example, by means of an aluminoxane into a polymerization-active cationic metallocene complex (EP-A-0129368).

The synthesis of metallocenes is known (U.S. Pat. No. 4,752,597; US 5,017,714; US 5,103,030; EP-A-0336128; EP-A-0387690; EP-A-0530647; EP-P-05307686; EP-A-0549900; H.-H. Brintzinger, D. Fischer, R. Mülhaupt, B. Rieger and R. Waymouth, Angew. Chem., 107 (1995) 1255; Angew. Chem. Int. Ed. Engl., 34 (1995) 1143; M. Aulbach and F. Küber, ChiùZ, 28 (1994) 197). For this purpose, metal compounds, e.g. metal alkoxides or metal halides such as $TiCl_4$, $ZrCl_4$, $HfCl_4$, can be reacted with a variety of cyclopentadienyl-metal compounds. This results in formation of considerable amounts of inorganic by-products (e.g. salts) which are mixed with the metallocene. When metallocenes are used as catalysts for the polymerization of olefins, these inorganic by-products have an adverse effect on the catalyst activity. To apply metallocene catalysts to a support, the metallocenes are generally activated by means of a cocatalyst and applied as a solution in a nonpolar solvent to a solid support. Here too, a low content of inorganic by-products in the metallocene used is, advantageous.

The separation of metallocene and inorganic by-products is usually carried out by dissolving the metallocene in organic solvents, which enables the inorganic by-products to be separated off as sparingly soluble components. Toluene and dichloromethane or other solvents such as tetrahydrofuran, diethyl ether, aliphatic, aromatic and chlorinated hydrocarbons are particularly frequently used as solvents for this purpose.

The organometallic by-products are usually separated off in a second step. Here, the crude product is dissolved in a solvent and the concentration of undesirable organometallic by-products, e.g. isomers, is reduced by subsequent fractional crystallization or fractional precipitation.

Disadvantages of these methods are that many metallocenes have only a moderate solubility in customary organic solvents and for this reason large amounts of solvents, large filtration apparatuses and a great deal of time are required. In addition, large amounts of toxic or environmentally problematical solvents are often used. Since the inorganic by-products are often obtained in very finely divided form, filtration times can become very long even when filter aids are added and filtration is carried out under pressure. To be able to isolate the metallocene as completely as possible from the filtrate, the solvent generally has to be distilled off. In this case, the problem of the limited stability of such metallocene solutions in the presence of impurities such as traces of moisture, bases, protic compounds and thermal stressing arises. A further point is that the large number of reaction steps can be uneconomical. This is made worse by the fact that the compounds formed in the individual purification steps, which sometimes comprise starting materials, cannot be isolated since they are in the form of mixtures of components which are difficult to separate from one another.

Although methods of reducing the concentration of inorganic and organometallic by-products are described in EP-A 0780396, economical recovery of the starting materials used is not possible; in particular, the valuable ligands cannot be isolated again.

It is an object of the present invention to provide a simple, mild and effective process for reducing the concentration of inorganic and organometallic by-products in product mixtures obtained in the synthesis of metallocenes, which process at the same time allows economical recovery of the starting materials used, in particular the ligands, and enables the large number of reaction steps to be dispensed with.

A process for separating inorganic and organometallic by-products from a mixture comprising at least one organometallic transition metal compound as product and at least one organometallic by-product and at least one inorganic by-product as by-products, which comprises the steps A) admixing the mixture comprising the product, the organometallic by-product and the inorganic by-product with a mixture comprising at least one polar organic extractant and water and separating off the undissolved residue, B) washing the residue from step A) with a nonpolar organic extractant or a mixture comprising at least one nonpolar organic extractant and at least one aprotic polar organic solvent and C) drying the residue which has been washed in step B) and comprises the organometallic transition metal compound.

The process of the present invention enables the organometallic transition metal compounds isolated in step C) to be obtained in high purity. The purity is generally at least 90% by weight, preferably at least 96% by weight. The proportion of inorganic by-products is preferably 5% by weight or less, particularly preferably 2% by weight or less.

As organometallic transition metal compounds, preference is given to using metallocene compounds. These can be, for example, bridged or unbridged biscyclopentadienyl complexes as are described, for example in EP-A-0 129 368, EP-A-0 561 479, EP-A-0 545 304 and EP-A-0 576 970, monocyclopentadjenyl complexes, multinuclear cyclopentadienyl complexes as described, for example, in EP-A-0 632 083, π-ligand-substituted tetrahydropentalenes as described, for example, in EP-A-0 659 758 or π-ligand-substituted tetrahydroindenes as described, for example, In EP-A-0 661 300. It Is also possible to use metallocene compounds whose complexing ligand contains heterocycles. Examples of such compounds are described in WO 98/22486.

Metallocene compounds used are preferably bridged compounds of the Formula (II),

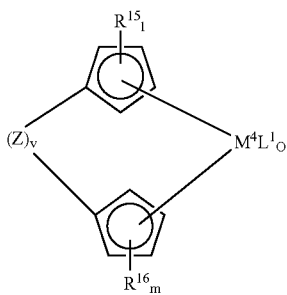

(II)

where
- $M^4$ is a metal of groups 3, 4, 5 or 6 of the Periodic Table of the Elements, in particular Ti, Zr or Hf, particularly preferably Zr,
- $R^{15}$ are Identical or different and are each a hydrogen atom or $Si(R^{17})_3$, where $R^{17}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_8$–$C_{20}$-aryl, $C_8$–$C_{10}$-fluoroaryl, $C_6$–$C_{10}$-aryloxy, $C_2$-$C_{10}$-alkenyl, $C_7$–$C_{40}$-arylalkyl, $C_7$–$C_{40}$-alkylaryl or $C_8$–$C_{40}$-arylalkenyl, or $R^{15}$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl. $C_3$–$C_{15}$-alkylalkenyl, $C_8$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_8$–$C_{24}$-aryl, fluorinated $C_7$–$C_{30}$-arylalkyl, fluorinated $C_7$–$C_{20}$-alkylaryl or $C_1$–$C_{12}$-alkoxy, or two or more radicals $R^{15}$ may be jointed to one another so that the radicals $R^{15}$ and the atoms of the cyclopentadienyl ring which connect them form a $C_4$–$C_{24}$ ring system which may in turn be substituted,
- $R^{16}$ are identical or different and are each a hydrogen atom or $Si(R^{16})_3$, where $R^{16}$ are identical or different and are each a hydrogen atom of a $C_1$–$C_{40}$ group, preferably $C_1$–$C_{20}$-alkyl, $C_1$–$C_{10}$-fluoroalkyl, $C_1$–$C_{10}$-alkoxy, $C_8$–$C_{14}$-aryl, $C_8$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^{16}$ is a $C_1$–$C_{25}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^{16}$ may be joined to one another so that the radicals $R^{16}$ and the atoms of the cyclopentadienyl ring which connect them form a $C_4$–$C_{24}$ ring system which may in turn be substituted,
- l is 4,
- m is 4,
- $L^1$ may be identical or different and are each a hydrogen atom, a $C_1$–$C_{10}$-hydrocarbon group such as $C_1$–$C_{10}$-alkyl or $C_6$–$C_{10}$-aryl, a halogen atom or $OR^{19}$, $SR^{19}$, $OSi(R^{19})_3$, $Si(R^{19})_3$, $P(R^{19})_2$ or $N(R^{19})_2$, where $R^{19}$ is a $C_1$–$C_{10}$-alkyl group, a halogenated $C_1$–$C_{10}$-alkyl group, a $C_6$–$C_{20}$-aryl group, a $C_7$–$C_{20}$-alkylaryl group or a halogenated $C_6C_{20}$-aryl group, or $L^1$ is a toluenesulfonyl, trifluoroacetyl, trifluoroacetoxyl, trifluoromethanesulfonyl, nonafluorobutanesulfonyl or 2,2,2-trifluoroethanesulfonyl group,
- o is an integer from 1 to 4, preferably 2,
- Z is a bridging structural element between the two cyclopentadienyl rings and v is 1.

Examples of Z are $M^5R^{20}R^{21}$ groups, where $M^5$ is carbon, silicon, germanium or tin and $R^{20}$ and $R^{21}$ are identical or different and are each hydrogen or a $C_1$–$C_{20}$-hydrocarbon-containing group such as $C_1$–$C_{10}$-alkyl, $C_6$–$C_{14}$-aryl or trimethylsilyl. Z is preferably $CH_2$, $CH_2$–$CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(CH_3)_3Si$—$Si(CH_3)(C_6H_5)_2Sn$, $(CH_2)_4Si$, $CH_2Si(CH_3)_2$, o-$C_6H_4$ or 2,2'-$(C_6H_4)_2$, or a 1,2-(1-methyl-ethanediyl), 1,2-(1,1-dimethylethanediyl) or 1,2(1,2-dimethylethanediyl) bridge. It is also possible for Z together with one or more radicals $R^{15}$ and/or $R^{16}$ to form a monocyclic or polycyclic ring system.

Preference is given to chiral bridged metallocene compounds of the Formula (II), in particular those in which v is 1 and one or two cyclopentadienyl rings are substituted so that they form an indenyl ring. The indenyl ring is preferably substituted, in particular in the 2 position, the 2,4 positions, the 2,4,5 positions, the 2,4,6 positions, the 2,4,7 positions or the 2,4,5,6 positions, by $C_1$–$C_{20}$ groups such as $C_1$–$C_{10}$-alkyl, $C_6$–$C_{20}$-aryl or $C_7$–$C_{20}$-alkylaryl, where two or more substituents on the indenyl ring may also together form a ring system.

In a particularly preferred embodiment of the process of the present invention, the organometallic transition metal compound desired as product is a compound of the Formula (II) in the racemic form. For the purposes of the present invention, the term racemic form also encompasses a form described as pseudo-racemic. This is the case when, for example, two indenyl ligands are in racemic positions relative to one another without taking account of all the other substituents.

Examples of metallocene compounds are:
dimethylsilanediylbis(indenyl)zirconium dichloride,
dimethylsilanediylbis(tetrahydroindenyl)zirconium dichloride,
ethylenebis(indenyl)zirconium dichloride,
ethylenebis(tetrahydroindenyl)zirconium dichloride,
dimethylsilanediylbis(2-methylindenyl)zirconium dichloride,
dimethylsilanediylbis(2-isopropylindenyl)zirconium dichloride,
diethylsilanediylbis(2-methylindenyl)zirconium dibromide,
dimethylsilanediylbis(2-ethylindenyl)zirconium dichloride,
dimethylsilanediylbis(2-methyl-4,5-benzindenyl)zirconium dichloride
dimethylsilanediylbis(2-ethyl-4,5-benzindenyl)zirconium dichloride
methylphenylsilanediylbis(2-methyl-4,5-benzindenyl)zirconium dichloride,
methylphenylsilanediylbis(2-ethyl-4,5-benzindenyl)zirconium dichloride,
diphenylsilanediylbis(2-methyl-4,5-benzindenyl)zirconium dichloride,
diphenylsilanediylbis(2-ethyl-4,5-benzindenyl)zirconium dichloride,
diphenylsilanediylbis(2-methylindenyl)hafnium dichloride,
dimethylsilanediylbis(2-methyl-4-phenylindenyl)zirconium dichloride,
dimethylsilanediylbis(2-ethyl-4-phenylindenyl)zirconium dichloride,
dimethylsilanediyl-(2-methyl-4-phenylindenyl)-(2,5-dimethyl-N-phenyl-4-azapentalene)zirconium dichloride,
dimethylsilanediylbis(3-tert-butyl-5-methylcyclopentadienyl)zirconium dichloride, dimethylsilanediylbis(3-tert-butyl-5-ethylcyclopentadienyl) zirconium dichloride,
dimethylsilanediylbis(2-methyl-4-(1-naphthyl)indenyl)zirconium dichloride,
dimethylsilanediylbis(2-ethyl-4-(1-naphthyl)indenyl)zirconium dichloride,
dimethylsilanediylbis(2-propyl-4-(1-naphthyl)indenyl)zirconium dichloride,
dimethylsilanediylbis(2-i-butyl-4-(1-naphthyl)indenyl)zirconium dichloride,
dimethylsilanediylbis(2-methyl-4-isopropylindenyl)zirconium dichloride,
dimethylsilanediylbis(2,7-dimethyl-4-isopropylindenyl)zirconium dichloride,
dimethylsilanediylbis(2-methyl-4,6-diisopropylindenyl)zirconium dichloride,
dimethylsilanediylbis(2-methyl-4[p-trifluoromethylphenyl]indenyl)zirconium dichloride,
dimethylsilanediylbis(2-methyl-4-[4'-tert-butylphenyl]indenyl)zirconium dichloride,
Diethylsilanediylbis(2-methyl-4-[4'-tert-butylphenyl]indenyl)zirconium dichloride,
dimethylsilanediylbis(2-ethyl-4-[4'-tert-butylphenyl]indenyl)zirconium dichloride,
dimethylsilanediylbis(2-propyl-4-[4'-tert-butylphenyl]indenyl)zirconium dichloride,
dimethylsilanediylbis(2-isopropyl-4-[4'-tert-butylphenyl]indenyl)zirconium dichloride,
dimethylsilanediylbis(2-n-butyl-4-[4'-tert-butylphenyl]indenyl)zirconium dichloride,
dimethylsilanediylbis(2-hexyl-4-[4'-tert-butylphenyl]indenyl)zirconium dichloride,
dimethylsilanediylbis(2-isopropyl-4-phenylindenyl)zirconium dichloride,
dimethylsilanediyl(2-isopropylindenyl)-(2-methyl-4-[4'-tert-butylphenyl]indenyl)zirconium dichloride,
dimethylsilanediyl(2-isopropylindenyl)-(2-methyl-4-(1-naphthyl)indenyl)zirconium dichloride,
dimethylsilanediyl(2-isopropylindenyl(2-methyl-4-phenylindenyl)zirconium dichloride,
dimethylsilanediyl(2-isopropyl-4-(1-naphthyl)indenyl)-(2-methyl-4-(1-naphthyl)-indenyl)zirconium dichloride,
dimethylsilanediyl(2-isopropyl-4-[4'-tert-butylphenyl]indenyl)-(2-methyl-4-phenyl-indenyl)zirconium dichloride,
dimethylsilanediyl(2-isopropyl-4-phenylindenyl)-(2-methyl-4-phenylindenyl)zirconium dichloride,
dimethylsilanediyl(2-isopropyl-4-[4'-tert-butylphenyl]indenyl)-(2-methyl-4-[4'-tert-butylphenyl]indenyl)zirconium dichloride,
dimethylsilanediyl(2-cyclohexyl-4-[4'-tert-butylphenyl]indenyl)-(2-methyl-4-[4'-tert-butylphenyl]indenyl)zirconium dichloride,
dimethylsilanediyl(2-cyclohexyl-4-[4'-tert-butylphenyl]indenyl)-(2-methyl-4-phenylindenyl)zirconium dichloride,
dimethylsilanediyl(2-isopropyl-4-[4'-tert-butylphenyl]indenyl)-(2-ethyl-4-[4'-tert-butylphenyl]indenyl)zirconium dichloride,
dimethylsilanediyl(2-isopropyl-4-[4'-tert-butylphenyl]indenyl)-(2-methyl-4-[3',5'-bis-tert-butylphenyl]indenyl)zirconium dichloride,
dimethylsilanediyl(2-isopropyl-4-[4'-tert-butylphenyl]indenyl)-(2-methyl-4-[1'-naphthyl]indenyl)zirconium dichloride,
dimethylsilanediyl(2-isopropyl-4-[1'-naphthyl]indenyl-(2-methyl-4-[4'-tert-butylphenyl]indenyl))zirconium dichloride,
ethylene(2-isopropyl-4-[4'-tert-butylphenyl]indenyl)-(2-methyl-4-[4'-tert-butylphenyl]indenyl)zirconium dichloride,
ethylenebis(2-isopropyl-4-[4'-tert-butylphenyl]indenyl)zirconium dichloride, 1,2-ethanediylbis(2-ethyl-4-phenylindenyl)zirconium dichloride,
1,2-ethanediylbis(2-methyl-4-[4'-tert-butylphenyl]indenyl)zirconium dichloride,
0,1,2-ethanediylbis(2-ethyl-4-[4'-tert-butylphenyl]indenyl)zirconium dichloride,
1,2-ethanediylbis(2-n-propyl-4-[4'-tert-butyl phenyl]indenyl)zirconium dichloride,
1,2-ethanediylbis(2-methyl-4-phenylindenyl)zirconium dichloride,
1,4-butanediylbis(2-methyl-4-phenylindenyl)zirconium dichloride,
1,4-butanediylbis(2-methyl-4,5-benzoindenyl)zirconium dichloride,
1,2-ethanediylbis(2-methyl-4,5-benzoindenyl)zirconium dichloride,
dimethylsilanediylbis(2-methyl-4-(4-methoxyphenylindenyl)zirconium dichloride,
dimethylsilanediylbis(2-n-propyl-4-phenyl)indenyl)zirconium dichloride,
dimethylsilanediyl(2-isopropyl-4-[4'-tert-butylphenyl]indenyl)-(2-methylindenyl)zirconium dichloride,
dimethylsilanediyl(2-isopropyl-4-[4'-tert-butylphenyl]indenyl)(2-ethylindenyl)zirconium dichloride,
dimethylsilanediyl(2-methyl-4-[4'-tert-butylphenyl]indenyl)-(2-isopropylindenyl)zirconium dichloride,
dimethylsilanediyl(2-ethyl-4-[4'-tert-butylphenyl]indenyl)$_2$-isopropylindenyl)zirconium dichloride,
dimethylsilanediyl(2-ethylpropyl-4-[4'-tert-butylphenyl]indenyl)-(2-methyl-4-[4'-tert-butylphenyl]indenyl)zirconium dichloride,
dimethylsilanediyl(2-ethylpropyl-4-[4'-tert-butylphenyl]indenyl)-(2-ethyl-4-[4'-tert-butylphenyl]indenyl)zirconium dichloride,
dimethylsilanediyl(2-sec-butyl-4-[4'-tert-butylphenyl]indenyl) (2-ethyl-4-[4'-tert-butylphenyl]indenyl)zirconium dichloride,
dimethylsilanediyl(2-sec-butyl-4-[4'-tert-butylphenyl]indenyl) (2-methyl-4-[4'-tert-butylphenyl]indenyl)zirconium dichloride,
dimethylsilanediyl(2-methylindenyl)-(2-isopropylindenyl)zirconium dichloride,
dimethylsilanediyl(2-ethylindenyl)-(2-isopropylindenyl)zirconium dichloride,
dimethylsilanediyl(2-ethylpropyl-4-[4'-tert-butylphenyl]indenyl)-(2-methylindenyl)zirconium dichloride,
dimethylsilanediyl(2-ethylpropyl-4-[4'-tert-butylphenyl]indenyl)-(2-ethylindenyl)zirconium dichloride,
dimethylsilanediyl(2-sec-butyl-4-[4'-tert-butylphenyl]indenyl)-(2-ethylindenyl)zirconium dichloride,
dimethylsilanediyl(2-sec-butyl-[4'-tert-butylphenyl]indenyl) (2-methylindenyl)zirconium dichloride,
dimethylsilanediyl(2-isopropyl-4-[4'-tert-butylphenyl]indenyl)-(2-methyl-4-[3',5'-bis-tert-butyl-4'-methoxyphenyl-]indenyl)zirconium dichloride,
dimethylsilanediyl(2 isopropyl-4-[4'-tert-butylphenyl]indenyl)-(2-ethyl-4-[3',5'-bis-tert-butyl-4'-methoxyphenyl-]indenyl)zirconium dichloride,
$C_4H_8$-silanediyl(2-isopropyl-4-[4'-tert-butylphenyl]indenyl)-(2-methyl-4-[4'-tert-butylphenyl]indenyl)zirconium dichloride,
$C_4H_8$-Silanediyl(2-isopropyl-4-[4'-tert-butylphenyl]indenyl)$_2$-ethyl-4-[4'-tert-butylphenyl]indenyl)zirconium dichloride, C₄H₈-silanediyl(2-isopropyl-4-[4'-tert-butylphenyl]indenyl)-(2-methyl-4-[3',5'-bis-tert-butyl-4'-methoxyphenyl-]indenyl)zirconium dichloride, C₄H₈-silanediyl(2-isopropyl-4-[4'-tert-butylphenyl]indenyl)-(2-ethyl-4-[3',5'-bis-tert-butyl-4'-methoxyphenyl]indenyl)zirconium dichloride.

The corresponding dimethylzirconium compounds and the corresponding η⁴-butadienezirconium compounds are also preferred.

For the purposes of the present invention, the term "organometallic by-product" refers to all organometallic compounds containing the same metal as the desired metallocene; at least one carbon-containing ligand, in particular a π-ligand, is bound to this metal. The meso form of the desired metallocene is likewise referred to as an organometallic by-product.

An exception from the definition of organometallic by-product is the desired metallocene itself in racemic form, which is to be concentrated or purified.

For example, the term "organometallic by-product" encompasses metallocenes which are isomers of the desired metallocene, other metallocenes which are not isomeric with the desired metallocene, organometallic compounds which are formed by incomplete reaction in the synthesis of the metallocene, oligomeric and polymeric reaction products and also compounds which are formed from the desired metallocene or one of the abovementioned by-products by reaction with impurities such as water, alcohols, amines, basic compounds or air or by thermal decomposition. The term "organometallic by-product" is also used when the desired product is present in the mixture in only a small proportion (for instance less than 50 percent by weight) and one or more of the constituents designated as "organometallic by-products" predominate in terms of amount.

Furthermore, the term "organic by-products" encompasses all organic compounds which are later bound to the metal. These are, for example, carbon-containing ligands, in particular π-ligands, and their precursors, in particular indenyls.

Organic byproducts are, in particular, the π-ligand of the formula (IIa) or double bond isomers thereof,

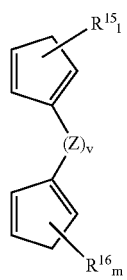

(IIa)

where Z, v, l, m, R¹⁵ and R¹⁶ are as defined under Formula (II).

The term "inorganic by-product" refers, for example, to inorganic salts or covalent metal halides (e.g. fluorides, chlorides, bromides or iodides). The inorganic salts have, for example, the formula (I)

$$M^2X^2_o \qquad (I),$$

where $M^2$ is a metal of group 1, 2, 3, 4, 12 or 13 of the Periodic Table of the Elements, preferably Li, Na, K, Mg, Ti, Zr, Hf or Ca, particularly preferably Li, Zr or Na, $X^2$ are identical or different and are each a halogen atom such as fluorine, chlorine, bromine or iodine, preferably chlorine, bromine or iodine, particularly preferably chlorine, or half an oxygen atom and o corresponds to the valency of $M^2$ and is 1, 2, 3 or 4.

Examples of salts of the formula (I) are LiF, LiCl, LiBr, LiI, NaF, NaCl, NaBr, NaI, KF, KCl, KBr, KI, CaF₂, CaCl₂, CaBr₂, CaI₂, CsF, CsCl, CsBr, CsI, MgF₂, MgCl₂, MgBrCl, BaCl₂, BaI₂, AlF₃, AlCl₃, AlBrCl₂, ZnCl₂, ZnBr₂, CdCl₂, CdBrI.

Examples of covalent metal halides are halides of metals of groups 3 or 4, in particular group 4, of the Periodic Table of the Elements, e.g. TiCl₄, ZrCl₄ or HfCl₄, or their oxides or oxychlorides.

The term "inorganic by-product" is also employed when the organometallic transition metal compound desired as product is present in the mixture in only a small proportion (for instance less than 50 percent by weight) and one or more of the constituents designated as "inorganic by-products" predominate in terms of amount.

The term "polar organic extractant" as employed in step A) refers to polar organic solvents and also mixtures of various polar organic solvents, if desired together with at least one nonpolar organic solvent.

The term "polar extractant" refers to the mixture of at least one polar organic extractant and water.

The polar organic extractant comprises from 5 to 100% by volume, preferably from 25 to 100% by volume, in each case based on the total volume of the polar organic extractant, of one or more polar organic solvents and may further comprise small amounts of one or more nonpolar organic solvents. The polar organic extractant in step A) particularly preferably comprises from 60 to 100% by volume, in each case based on the total volume of the polar organic extractant, of one or more polar organic solvents and from 0 to 40% by volume of one or more nonpolar organic solvents.

As polar organic extractants, it is possible to use, for example, protic organic or aprotic organic solvents and mixtures thereof.

Examples of such polar organic solvents are alcohols such as methanol, ethanol, 1-propanol, 2-propanol, 1-butanol, 2-butanol, isobutanol, tert-butanol, 1-pentanol, 2-pentanol, 3-pentanol, amyl alcohol, isoamyl alcohol, 1-hexanol, 2-hexanol, 3-hexanol, 2-methyl-2-pentanol, 2-methyl-3-pentanol, 3-methyl-3-pentanol, 1-heptanol, 2-heptanol, 3-heptanol, 4-heptanol, 2-methyl-2-hexanol, 3-methyl-3-hexanol, 4-methyl-4-hexanol, 2-methyl-4-hexanol, 4-methyl-2-hexanol, 2-ethylhexanol, benzyl alcohol, phenol, resorcinol, 1-phenylethanol, 2-phenylethanol, 1-phenyl-2-butanol, 3-phenyl-1-butanol, 1,2-propanediol, 1,3-propanediol, 1,2-butanediol, 1,3-butanediol, 1,4-butanediol, ethylene glycol or glycerol, amines such as ethanolamine, propanolamine, methylamine, dimethylamine, trimethylamine, ethylamine, diethylamine, triethylamine, methylethylamine, methylbutylamine, propylamine, dipropylamine, tripropylamine, diisopropylamine, triisopropylamine, tert-butylamine, 1,2-ethylenediamine, N,N,N',N'-tetramethyl-1,2-ethylenediamine, di(n-butyl)amine, tributylamine, aniline, N-methylaniline, N,N-dimethylaniline, toluidine or N,N-dimethyltoluidine, aldehydes such as acetaldehyde, butyraldehyde, hexanal or propionaldehyde, ketones such as butanone, acetone, methyl propyl ketone or diethyl ketone, carboxylic acids such as formic acid, acetic acid, propionic acid, butyric acid, isobutyric acid, pentanoic acid or hexanoic acid, carboxylic esters such as methyl formate, ethyl formate, propyl formate, butyl formate, methyl acetate, ethyl acetate, propyl acetate, butyl acetate, methyl propionate or butyl propionate, ethers such as dimethyl ether, diethyl ether, methyl ethyl ether, dibutyl ether, diisopropyl ether, dioxane, trioxane, tetrahydrofuran, heteroaromatics such as furan, pyrrole, pyridine or thiophene, carboxamides such as formamide, dimethylformamide, diethylformamide, dimethylacetamide, diethylacetamide or N-methylpyrrolidone, nitriles such as acetonitrile, propionitrile or butyronitrile, haloaromatics such as chlorobenzene, 1,2-dichlorobenzene, 1,3-dichlorobenzene or bromobenzene, alkyl halides such as ethyl bromide, ethyl chloride, ethyl fluoride, butyl bromide, butyl chloride, methyl chloride or dichloromethane and nitro compounds such as nitromethane, nitroethane, 1-nitropropane, 2-nitropropane, 1-nitrobutane, 2-nitrobutane, nitrobenzene, 2-nitrotoluene or 3-nitrotoluene.

Aprotic polar organic solvents are, as understood by a person skilled in the art, polar organic solvents which are not able to form hydrogen bonds (Organikum, 15th revised edition, Berlin 1981, page 226).

The term "nonpolar organic extractant" as employed in step B) refers to nonpolar organic solvents or mixtures of various nonpolar organic solvents.

The nonpolar organic extractant comprises from 5 to 100% by volume, preferably from 25 to 100% by volume, in each case based on the total volume of the nonpolar organic extractant, of one or more nonpolar organic solvents and may further comprise small amounts of one or more polar organic solvents. The nonpolar organic extractant particularly preferably comprises from 60 to 100% by volume, in each case based on the total volume of the nonpolar organic extractant, of one or more nonpolar organic solvents and from 0 to 40% by volume of one or more polar organic solvents.

Examples of nonpolar organic solvents are alkanes such as propane, butane, isobutane, pentane, 2-methylbutane, neopentane, cyclopentane, hexane, 2-methylpentane, 3-methylpentane, heptane, 2-methylhexane, 3-methylhexane, cyclohexane, octane, isooctane, nonane, isononane or decane and aromatic hydrocarbons such as benzene, toluene or xylene.

Preferred polar organic extractants, particularly in step A), are methanol, ethanol, 2-butanol, isobutanol, acetone, dichloromethane, pentane/methanol, pentane/ethanol, hexane/2-butanol, heptane/isobutanol, octane/acetone or heptane/toluene/isobutanol. Here, the proportion by volume of all polar organic solvents present in each case is from 5 to 100%, preferably from 25 to 100%, particularly preferably from 60 to 100%. Particularly preferred polar organic extractants are ethanol, isobutanol, acetone, heptane/isobutanol, heptane/toluene/isobutanol.

In a particularly preferred embodiment, the present invention provides a process for separating inorganic by-products of the formula (I) and organometallic by-products of the Formula (II) as meso form from a mixture comprising, as product, organometallic transition metal compounds of the Formula (II) in the racemic form. The chiral bridged metallocene compounds of the Formula (II) can be present as rac/meso mixtures in various ratios. The mixture is preferably the crude product obtained directly in the synthesis of the metallocene. However, the crude product can also have been pretreated, e.g. with solvents. This mixture comprises the organometallic products of the Formula (II) in the rac/meso ratio obtained in their preparation.

In a preferred embodiment of the process, the liquid phase from step B) can be worked up in a further step D) to recover the organic starting materials, in particular the organic ligand systems of the formula (IIa), and the ligand system can be isolated.

In the process of the present invention, one or more inorganic by-products (e.g. inorganic salts or covalent metal halides) go into solution in the chosen extractant, which is a mixture comprising at least one polar organic extractant and water, in step A). The desired metallocene remains as a solid and can be isolated by, for example, filtration, centrifugation or decantation. This makes it possible to separate the undesirable inorganic by-products from the desired metallocene under mild conditions in a short time, using relatively small amounts of extractant. The space-time yield of the process of the present invention is high. In addition, the separation times (e.g. filtration times) can be greatly reduced by means of the process of the present invention, so that even large amounts of metallocenes can be purified simply, quickly and inexpensively.

The molar ratios of extractants added depend on the degree of contamination with inorganic and organometallic and also organic impurities.

The molar ratio of the polar organic extractant to water is from 100:1 to 1:100, preferably from 10:1 to 1:10, particularly preferably from 2:1 to 1:2.

The process of the present invention can, for example, be carried out by suspending the crude product obtained in the metallocene synthesis, which comprises at least one metallocene and at least one inorganic by-product, in a mixture comprising at least one polar organic extractant and water at from −100 to +200° C., preferably from −10 to +100° C., particularly preferably from 20 to +50° C., and mixing vigorously. The polar organic extractant comprises at least one polar organic solvent or a mixture of various polar organic solvents or a mixture of one or more polar organic solvents and one or more nonpolar organic solvents. The crude product can be treated directly with the polar extractant which comprises water and the polar organic extractant. If a mixture of polar and, if desired, nonpolar organic solvents and water is to be used, the individual solvents can also be brought into contact with the crude product successively, for example firstly the nonpolar solvent and then the polar organic solvent and water or vice versa. During the contact time with the polar extractant, which can be from 1 minute to 96 hours, preferably between 10 minutes and 8 hours, the inorganic by-products go into solution. The temperature is selected so that the organometallic transition metal compounds of the Formula (II) are present as solids suspended in the liquid phase, i.e. they do not go into solution. The subsequent temperature is in a preferred range from 20° C. to 150° C. Furthermore, the treatment can be carried out at atmospheric pressure. However, it can also be carried out at superatmospheric pressure, although this requires appropriate reactors. The molar stoichiometric ratio in which the compounds of the Formula (II) and of the formula (I) are combined with the polar organic extractants is from 1:1000 to 1:0.01, preferably from 1:100 to 1:1.

The solid which remains is subsequently separated from the solution, e.g. by filtration, centrifugation or decantation. In this way, the dissolved inorganic by-products are separated off.

The product obtained as solid comprises the metallocene. The process of the present invention generally leads to a reduction in the concentration of the inorganic by-products in the mixture which has been treated with the polar extractant to below 5% by weight, based on the total amount of the product obtained in solid form. Reductions in the concentration of inorganic by-products to below 0.1% by weight can also be achieved, in particular when the treatment of the mixture with a polar extractant in step A) is repeated one or more times.

After isolation of the enriched organometallic transition metal compound of the Formula (II), a further washing step is carried out in step B). Here, the concentration of organometallic and undesirable organic compounds is reduced by means of a nonpolar organic extractant or a mixture comprising at least one nonpolar organic extractant and at least one aprotic polar organic solvent.

The filtrate from step B) represents the liquid phase for the recovery step D) for the organic compounds, in particular the ligand system of the formula (IIa) present in this phase.

The treatment in step B) is carried out for from 1 minute to 96 hours. Preference is given to from 10 minutes to 8 hours. The temperature of the initial charge when the extractant is added is from −100° C. to 200° C., preferably from −80° C. to 150° C., particularly preferably from 20° C. to 100° C. The temperature is selected so that the desired organometallic transition metal compounds of the Formula (II) are present as solid suspended in the liquid phase, i.e. they do not go into solution. The subsequent temperature is in a preferred range from 20° C. to 150° C. Furthermore, the treatment is carried out at atmospheric pressure. However, it can also be carried out at superatmospheric pressure, although this requires appropriate reactors. The molar ratio in which the compounds of the Formula (II) and the nonpolar organic extractant or mixture of aprotic polar solvent and nonpolar organic extractant are combined is from 1:1000 to 1:0.01. A stoichiometric ratio from 1:100 to 1:1 is preferred.

The liquid phase from step B) comprises, in particular, unreacted ligand systems of the formula (IIa) or the ligand system from the meso form of the metallocene of the Formula (II) which is depleted through decomposition.

To isolate the ligand systems of the formula (IIa) from the washing solution from step B), this liquid phase, i.e. the washing solution, is worked up in a further process step D), i.e. the solvent is removed or reduced. Crystallization in particular enables considerable amounts of the ligand system to be recovered, i.e. isolated. This has not been possible by means of the methods known hitherto.

The organic compounds which have been isolated do not have to be purified by means of a further process step and can be used for further reactions, for example for the preparation of metallocenes.

In one variant of the process of the present invention for separating off by-products and recovering the ligands, steps A) and B) can be combined. In this case, the polar extractant for step A) is used simultaneously with the extractant for step B). The recovery of the ligand system from this washing solution can be carried out using the following method. The mixture present in the liquid phase (washing solution) is firstly isolated as a solid by removing the liquid constituents. This solid comprises the ligand system together with further organic by-products and inorganic by-products. This solid which has been isolated can be fractionated by sequential use of the solvents of steps A) and B) and the ligand system of the formula (IIa) or its double bond isomers can be recovered from the second liquid phase by means of the process step D).

The following examples illustrate the invention, but do not limit it in any way. Only 1:1 rac/meso mixtures of the complexes were used.

EXAMPLE 1

In a 2000 ml two-necked flask provided with a magnetic stirrer bar, 130 g of rac/meso-dimethylsilanediyl(2-methyl-4-(4'-tert-butylphenyl)indenyl)(2-isopropyl-4-(4'-tert-butylphenyl)-indenyl)zirconium dichloride containing 31.2 g of lithium chloride were suspended in 1600 ml of acetone and 347 ml of water and the mixture was stirred at an internal temperature of 40° C. for 100 minutes. The residue was subsequently separated off by a G3 frit. The filtrate was discarded. The filter cake was subsequently washed twice with a total of 200 ml of a toluene/THF mixture (volume ratio 9:1). The yellow residue was then dried to constant weight at room temperature in an oil pump vacuum. This gave 40.5 g of rac-dimethylsilanediyl(2-methyl-4-(4'-tert-butylphenyl)indenyl)(2-iso-propyl-4-(4'-tert-butylphenyl)indenyl)zirconium dichloride, rac/meso 30:1, as a yellow solid.

LiCl Content: <0.1%

Crystallization of the second filtrate gave 32 g of the ligand dimethylsilanediyl (2-methyl-4-(4'-tert-butylphenyl)indene)(2-isopropyl-4-(4'-tert-butylphenyl)indene), corresponding to 69% of the possible ligand from the meso compound.

EXAMPLE 2

In a 2000 ml two-necked flask provided with a magnetic stirrer bar, 130 g of rac/meso-dimethylsilanediyl(2-ethyl-4-(4'-tert-butylphenyl)indenyl)(2-isopropyl-4-(4'-tert-butylphenyl)-indenyl)zirconium dichloride containing 29.2 g of lithium chloride were suspended in 1500 ml of acetone and 300 ml of water and the mixture was stirred at an internal temperature of 40° C. for 100 minutes. The residue was subsequently separated off by a G3 frit. The filtrate was discarded. The filter cake was subsequently washed twice with a total of 200 ml of a toluene/THF mixture (volume ratio 9:1). The yellow residue was then dried to constant weight at room temperature in an oil pump vacuum. This gave 38.5 g of rac-dimethylsilanediyl(2-ethyl-4-(4'-tert-butylphenyl)indenyl)(2-iso-propyl-4-(4'-tert-butylphenyl)indenyl)zirconium dichloride, rac/meso 50:1, as a yellow solid.

LiCl Content: <0.3%

Crystallization of the second filtrate gave 37 g of the ligand dimethylsilanediyl (2-ethyl-4-(4'-tert-butylphenyl)indene)(2-isopropyl-4-(4'-tert-butylphenyl)indene), corresponding to 73% of the possible ligand from the meso compound.

EXAMPLE 3

In a 2000 ml two-necked flask provided with a magnetic stirrer bar, 100 g of rac/meso-dimethylsilanediyl(2-methyl-4-(4'-tert-butylphenyl)indenyl)(2-isopropyl-4-(naphthyl)indenyl)-zirconium dichloride containing 24.0 g of lithium chloride were suspended in 1400 ml of acetone and 304 ml of water and the mixture was stirred at an internal temperature of 40° C. for 100 minutes. The residue was subsequently separated off by a G3 frit. The filtrate was discarded. The filter cake was subsequently washed twice with a total of 200 ml of a toluene/THF mixture (volume ratio 9:1). The yellow residue was then dried to constant weight at room temperature in an oil pump vacuum. This gave 27.9 g of rac-dimethylsilanediyl(2-methyl-4-(4'-tert-butylphenyl)indenyl)(2-isopropyl-4-(naphthyl)indenyl)zirconium dichloride, rac/meso 25:1, as a yellow solid.

Crystallization of the second filtrate gave 28 g of the ligand dimethylsilanediyl (2-methyl-4-(4'-tert-butylphenyl)indene)(2-isopropyl-4-(naphthyl)indene), corresponding to 73% of the possible ligand from the meso compound.

EXAMPLE 4

In a 2000 ml two-necked flask provided with a magnetic stirrer bar, 110 g of rac/meso-dimethylsilanediyl(2-methyl-4-(4'-tert-butylphenyl)indenyl)(2-cyclohexyl-4-(4'-tert-butylphenyl)-indenyl)zirconium dichloride containing 22 g of lithium chloride were suspended in 1400 ml of acetone and 304 ml of water and the mixture was stirred at an internal temperature of 40° C. for 100 minutes. The residue was subsequently separated off by a G3 frit. The filtrate was discarded. The filter cake was subsequently washed twice with a total of 200 ml of a toluene/DME mixture (volume ratio 9:1). The yellow residue was then dried to constant weight at room temperature in an oil pump vacuum. This gave 30.7 g of rac-dimethylsilanediyl(2-methyl-4-(4'-tert-butylphenyl)indenyl)(2-cyclohexyl-4-(4'-tert-butylphenyl)indenyl)zirconium dichloride, rac/meso 30:1, as a yellow solid.

LiCl Content: <1%

Crystallization of the second filtrate gave 20 g of the ligand dimethylsilanediyl (2-methyl-4-(4'-tert-butylphenyl)indene)(2-cyclohexyl-4-(4'-tert-butylphenyl)indene), corresponding to 57% of the possible ligand from the meso compound.

EXAMPLE 5

In a 2000 ml two-necked flask provided with a magnetic stirrer bar, 80 g of rac/meso-dimethylsilanediyl(2-methyl-4-phenyl)indenyl)(2-isopropyl-4-phenyl)indenyl)zirconium dichloride containing 16 g of lithium chloride were suspended in 900 ml of acetone and 196 ml of water and the mixture was stirred at an internal temperature of 40° C. for 60 minutes. The residue was subsequently separated off by a G3 frit. The filtrate was discarded. The filter cake was subsequently washed twice with a total of 200 ml of a toluene/THF mixture (volume ratio 9:1). The yellow residue was then dried to constant weight at room temperature in an oil pump vacuum. This gave 23.7 g of rac-dimethylsilanediyl(2-methyl-4-phenyl)indenyl)(2-isopropyl-4-phenyl)indenyl)zirconium dichloride, rac/meso 30:1, as a yellow solid.

LiCl Content: <0.1%

Crystallization of the second filtrate gave 12.9 g of the ligand dimethylsilanediyl(2-methyl-4-phenyl)indene)(2-isopropyl-4-(phenyl)indene), corresponding to 53% of the possible ligand from the meso compound.

EXAMPLE 6

In a 4000 ml two-necked flask provided with a magnetic stirrer bar, 200 g of rac/meso-dimethylsilanediylbis(2-methyl-4,5-benzindenyl)zirconium dichloride containing 48 g of lithium chloride were suspended in 2700 ml of acetone and 588 ml of water and the mixture was stirred at an internal temperature of 40° C. for 100 minutes. The residue was subsequently separated off by a G3 frit. The filtrate was discarded. The filter cake was subsequently washed twice with a total of 400 ml of a toluene/DME mixture (volume ratio 9:1). The yellow residue was then dried to constant weight at room temperature in an oil pump vacuum. This gave 52.9 g of rac-dimethylsilanediylbis(2-methyl-4,5-benzindenyl)zirconium dichloride, rac/meso 30:1, as a yellow solid.

LiCl Content: <1%

Crystallization of the second filtrate gave 45.7 g of the ligand dimethylsilanediylbis(2-methyl-4,5-benzindene), corresponding to 83% of the possible ligand from the meso compound.

EXAMPLE 7

In a 4000 ml two-necked flask provided with a magnetic stirrer bar, 200 g of rac/meso-dimethylsilanediylbis(2-methyl-4-phenylindenyl)zirconium dichloride containing 24 g of lithium chloride were suspended in 2200 ml of acetone and 480 ml of water and the mixture was stirred at an internal temperature of 25° C. for 30 minutes. The residue was subsequently separated off by a G3 frit. The filtrate was discarded. The filter cake was subsequently washed twice with a total of 400 ml of a toluene/DME mixture (volume ratio 9:1). The yellow residue was then dried to constant weight at room temperature in an oil pump vacuum. This gave 57.3 g of rac-dimethylsilanediylbis(2-methyl-4-phenylindenyl)zirconium dichloride, rac/meso 30:1, as a yellow solid.

LiCl Content: <0.3%

Crystallization of the second filtrate gave 51.7 g of the ligand dimethylsilanediylbis(2-methyl-4-phenylindene), corresponding to 78% of the possible ligand from the meso compound.

We claim:
1. A process for separating inorganic and organometallic by-products from a mixture comprising at least one organometallic transition metal compound as product and at least one organometallic by-product and at least one inorganic by-product as by-products, which comprises the steps
A) admixing the mixture comprising the product, the organometallic by-product and the inorganic by-product with a mixture comprising at least one polar organic extractant and water, wherein the molar ratio of the polar organic extractant to water is from 10:1 to 1:10, and separating off the undissolved residue,
B) washing the residue from step A) with a nonpolar organic extractant or a mixture comprising at least one nonpolar organic extractant and at least one aprotic polar organic solvent and
C) drying the residue which has been washed in step B) and comprises the organo-metallic transition metal compound,
wherein the organometallic transition metal compound is a compound of the formula (II) in racemic form

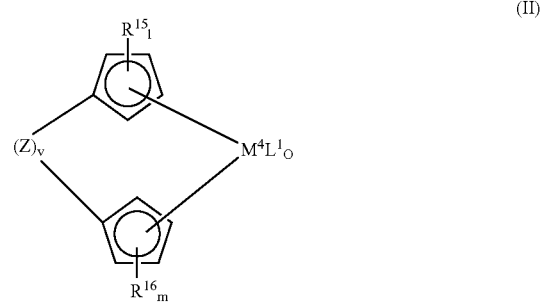

(II)

where

M⁴ is a metal of groups 3, 4, 5 or 6 of the Periodic Table of Element, $R^{15}$ are identical or different and are each a hydrogen atom or $Si(R^{17})_3$, where $R^{17}$ are identical or different and are each a hydrogen atom of a $C_1–C_{40}$ group, or $R^{15}$ is a $C_1–C_{30}$ group, or two or more radicals $R^{15}$ may be jointed to one another so that the radicals $R^{15}$ and the atoms of the cyclopentadienyl ring which connect them form a $C_4–C_{24}$ ring system which may in turn be substituted, $R^{16}$ are identical or different and are each a hydrogen atom or a $Si(R^{18})_3$ $R^{18}$ are identical or different and are each a hydrogen atom or a $C_1–C_{40}$ group, or $R^{16}$ is a $C_1–C_{30}$ group, or two or more radicals $R^{16}$ may be joined to one another so that the radicals $R^{16}$ and the atoms of the cyclopentadienyl ring which connect them form a $C_4–C_{24}$ ring system which may in turn be substituted, l is 4, m is 4, $L^1$ are identical or different and are each a hydrogen atom, a $C_1–C_{10}$-hydrocarbon group, a halogen atom, $OR^{19}$, $SR^{19}$, $OSi(R^{19})_3$, $Si(R^{19})_3$, $P(R^{19})_2$ or $N(R^{19})_2$ where $R^{19}$ is a $C_1–C_{10}$-alkyl group, a halogenated $C_1–C_{10}$-alkyl group, a $C_6–C_{20}$-aryl group, a $C_7–C_{20}$-alkylaryl group or a halogenated $C_6–C_{20}$-aryl group, or $L^1$ is a toluenesulfonyl, trifluoroacetyl, trifluoroacetoxyl, trifluoromethane-sulfonyl, nonafluorobutanesulfonyl or 2,2,2-trifluoroethanesulfonyl group, o is an integer from 1 to 4, Z is a bridging structural element between the two cyclopentadienyl rings and v is 1.

2. A process as claimed in claim 1, wherein the inorganic by-product is a compound of the formula (I)

$$M^2X^2_o \quad (I)$$

where $M^2$ is a metal of group 1, 2, 3, 4, 12 or 13 of the Periodic Table of the Elements, $X^2$ are identical or different and are each a halogen atom or half an oxygen atom and o corresponds to the valency of $M^2$ and is 1, 2, 3 or 4.

3. A process as claimed in claim 1, wherein the polar organic extractant in step A) comprises from 60 to 100% by volume, in each case based on the total volume of the polar organic extractant, of one or more polar organic solvents and from 0 to 40% by volume of one or more nonpolar organic solvents.

4. A process as claimed in claim 1, wherein the polar organic extractants used in step A) are protic or aprotic organic solvents or mixtures thereof.

5. A process as claimed in claim 1, wherein polar extractants used are alcohols, amines, aldehydes, ketones, carboxylic acids, carboxylic esters, ethers, heteroaromatics, carboxamides, nitriles, haloaromatics, alkyl halides and nitro compounds.

6. A process as claimed in claim 1, wherein the nonpolar organic extractant comprises from 60 to 100% by volume, in each case based on the total volume of the nonpolar organic extractant, of one or more nonpolar organic solvents and from 0 to 40% by volume of one or more polar organic solvents.

7. A process as claimed in claim 1, wherein nonpolar solvents used are alkanes or aromatic hydrocarbons.

8. A process as claimed in claim 1, wherein polar organic extractants used in step A) are methanol, ethanol, 2-butanol, isobutanol, acetone, dichloromethane, pentane/methanol, pentane/ethanol, hexane/2-butanol, heptane/isobutanol, octane/acetone, acetone/water or heptane/toluene/isobutanol.

9. A process as claimed in claim 1, wherein the polar organic extractant in step A) is ethanol, isobutanol, acetone, heptane/isobutanol, heptane/toluene/isobutanol.

10. A process as claimed in claim 1, the process comprising additionally a step

D) isolating ligand systems of a formula (IIa) or their double bond isomers

(IIa)

where Z, v, l, m, $R^{15}$ and $R^{16}$ are as defined under formula (II) in claim 1 by working up the liquid phase obtained from step B) the liquid phase comprising, in particular organic ligand systems of the metallocene of the formula (II).

11. A process as claimed in claim 1, wherein step A) and step B) are carried out simultaneously, the solids dissolved in the liquid phases are isolated, the solid which has been isolated is fractionated by sequential use of the solvents of steps A) and B) and the process further comprises a step D) isolating ligand systems of a formula (IIa)

(IIa)

where Z, v, l, m, $R^{15}$ and $R^{16}$ are as defined under formula (II) in claim 1, or their double bond isomers by working up the liquid phase obtained from the second liquid phase comprising, in particular organic ligand systems of the metallocene of the formula (II).

* * * * *

UNITED STATES PATENT AND TRADEMARK OFFICE
CERTIFICATE OF CORRECTION

PATENT NO.          : 7,223,878 B2                                          Page 1 of 1
APPLICATION NO. : 10/478666
DATED                   : May 29, 2007
INVENTOR(S)         : Schulte et al.

It is certified that error appears in the above-identified patent and that said Letters Patent is hereby corrected as shown below:

In Claim 1, col. 15, indicated line 13:

"or a $Si(R^{18})_3$ $R^{18}$ are" should read -- or a $Si(R^{18})_3$ where $R^{18}$ are --

Signed and Sealed this

Eleventh Day of March, 2008

JON W. DUDAS
*Director of the United States Patent and Trademark Office*